United States Patent [19]

Ridland et al.

[11] Patent Number: 5,089,149

[45] Date of Patent: Feb. 18, 1992

[54] ORGANO-METALLIC COMPOUNDS

[75] Inventors: John Ridland, Wingate; David A. Brown, Cleveland, both of England

[73] Assignee: Tioxide Group plc, London, England

[21] Appl. No.: 444,812

[22] Filed: Dec. 1, 1989

[30] Foreign Application Priority Data

Dec. 16, 1988 [GB] United Kingdom ............... 8829401

[51] Int. Cl.$^5$ ............................ C09K 3/00; C07F 7/00
[52] U.S. Cl. ................................. 252/8.551; 556/51; 556/54; 166/283; 166/305.1; 166/308
[58] Field of Search ................ 556/51, 54; 166/308, 166/305.1, 283; 252/8.551

[56] References Cited

U.S. PATENT DOCUMENTS

| | | | |
|---|---|---|---|
| 4,348,498 | 9/1982 | Kamio et al. | 525/13 |
| 4,460,751 | 7/1984 | Hanlon et al. | 525/371 |
| 4,488,975 | 12/1984 | Almond | 252/8.55 R |
| 4,579,670 | 1/1986 | Payne | 252/8.55 R |
| 4,683,068 | 7/1987 | Kucera | 252/8.551 |
| 4,686,052 | 8/1987 | Baranet et al. | 252/8.551 |
| 4,797,216 | 1/1989 | Hodge | 252/8.551 |
| 4,798,902 | 1/1989 | Putzig | 556/54 |
| 4,861,500 | 8/1989 | Hodge | 252/8.551 |
| 4,953,621 | 9/1990 | Putzig et al. | 166/308 |
| 4,957,165 | 9/1990 | Cantu et al. | 166/295 |

FOREIGN PATENT DOCUMENTS

| | | |
|---|---|---|
| 0195531 | 9/1986 | European Pat. Off. |
| 3017887 | 11/1980 | Fed. Rep. of Germany. |
| 49-036630 | 4/1974 | Japan. |
| 49-094768 | 9/1974 | Japan. |
| 49-096046 | 9/1974 | Japan. |
| 51-041897 | 11/1976 | Japan. |
| 52-001737 | 1/1977 | Japan. |
| 52-038542 | 9/1977 | Japan. |
| 55-108423 | 8/1980 | Japan. |
| 55-149314 | 11/1980 | Japan. |
| 60-069166 | 4/1985 | Japan. |
| 62-046582 | 10/1987 | Japan. |
| 0789566 | 1/1958 | United Kingdom ............... 556/54 |
| 1029723 | 5/1966 | United Kingdom. |
| 2051093 | 1/1981 | United Kingdom. |

*Primary Examiner*—Jose G. Dees
*Assistant Examiner*—Porfirio Nazario
*Attorney, Agent, or Firm*—Banner, Birch, McKie & Beckett

[57] ABSTRACT

An organometallic compound which is the reaction product of (a) a zirconium halide or oxyhalide, (b) a polyol and (c) an alpha-hydroxy acid is claimed. The preferred polyol is sorbitol and preferred alphahydroxy acids are citric, malic or lactic acid. The compounds find use as cross-linking agents in fracturing fluids employed in the hydraulic fracturing of oil or gas-containing subterranean strata. The claimed compounds can be used to produce a slow or delayed gel formation in such fluids.

26 Claims, No Drawings

ORGANO-METALLIC COMPOUNDS

This invention relates to organo-metallic compounds and particularly to organo-zirconium compounds.

According to the present invention an organo-metallic compound comprises a reaction product of a zirconium halide or oxyhalide, a polyol and an alpha-hydroxy carboxylic acid.

According to the invention also a method for the manufacture of an organo-metallic compound comprises reacting a mixture of a polyol and an alpha hydroxy carboxylic acid with a zirconium halide or oxyhalide in solution and neutralising any acid by-product formed during the reaction.

Organo-metallic compounds according to the present invention have been found to be of use as cross-linking agents for so-called "fracturing" fluids used in the hydraulic fracturing process. In this process a cross-linked gel based on compounds such as guar gum and its derivatives containing a proppant such as sand, is forced down an oil well under pressure. This causes the dense hydrocarbon-bearing strata to fracture. The viscous fluid then breaks down and is recovered leaving behind the proppants to hold open the fractures which allow an increased flow of hydrocarbons to the well bore.

In hydraulic fracturing operations it is often desirable and sometimes necessary that the viscous treating fluids should have relatively low initial viscosities but that their viscosities should increase when they are placed in the subterranean formation to be treated.

The viscosity of the fluid must be low enough to ensure that excessive friction losses and high well head pumping pressure are not encountered but then, once in the formation, be high enough to both support the proppant particles and produce satisfactory subterranean fractures.

The organo-metallic compounds of the present invention are compounds of zirconium and more specifically are reaction products of a zirconium halide or oxyhalide, a polyol and an alpha-hydroxy carboxylic acid.

Although any appropriate halide or oxyhalide of zirconium can be used to prepare the compounds of the present invention zirconium tetrachloride is preferred.

The alpha-hydroxy acids useful in accordance with the invention can be monocarboxylic acids such as lactic acid and glycolic acid, dicarboxylic acids such as malic acid or tricarboxylic acids such as citric acid. Carboxylic acids having a plurality of hydroxy groups can be used provided that one of the groups is in the alpha position and examples of such hydroxy acids are gluconic acid and glyceric acid and polyhydroxy polycarboxylic acids such as tartaric acid or saccharic acid. Hydroxy aromatic acids such as mandelic acid can be used. Preferably the alpha-hydroxy acid is lactic acid, malic acid or citric acid. Mixtures of two or more alpha-hydroxy acids can be used if desired.

The polyol which is used to form the compounds of the present invention preferably contains at least three hydroxy groups and suitable polyols are the trihydric, tetrahydric, pentahydric or hexahydric alcohols. Examples of such polyols are glycerol, erythritol, arabitol, xylitol, sorbitol, dulcitol, mannitol and inositol. Monosaccharides, e.g. glucose, fructose, mannose, galactose, lactose and maltose can be used. The preferred polyol is sorbitol. Mixtures of two or more polyols can be used if desired.

The proportions of the three essential ingredients of the metallic compound of the present invention can vary widely but preferably amounts per mole of zirconium of alpha-hydroxy acid are from 2 to 6 moles, more preferably 2 to 4 moles but in relation to specific hydroxy acids are for malic acid from 2 to 4 moles, for lactic acid from 3 to 6 moles and for citric acid from 1.5 to 2.5 moles. Generally from 0.25 to 4 moles of polyol are preferred per mole of zirconium with specific preferred amounts for sorbitol of from 0.25 to 2 moles and for glycerol of from 0.5 to 4 moles.

Control in the reactivity of the cross-linker can be achieved by either varying the polyol level for a certain Zr/acid combination or by varying the alpha-hydroxycarboxylic acid level for a certain Zr/polyol combination. With this, the reactivity and hence gelling characteristics of fracturing fluids can be fine tuned to suit the final application. Furthermore, during the hydraulic fracturing process, a range of these compounds having different reactivities could be used to allow even greater control over the gel viscosities.

The reactivities of the compounds can be such that a significant build up in viscosity does not occur for a period between a few minutes and 1-2 hours. Furthermore the reactivity can be such that heat is required to produce the desired significant build up in viscosity. The temperature of gelation may then be controlled to suit the end user in the hydraulic fracturing process. This is desirable as often it is difficult to effectively control fracturing in the deeper, hotter wells even using conventional delayed cross-linking agents which can prematurely cross-link the fracturing fluid as temperatures rise near the bottom of the well bore.

The organo metallic compounds of the present invention can be obtained by reacting a mixture of a polyol and an alpha-hydroxy acid with a zirconium halide in solution and neutralising any acid by-products formed during the reaction. Usually the zirconium halide is reacted with a solution prepared by dissolving the alpha-hydroxy acid and the polyol in water. If desired this aqueous solution is rendered alkaline prior to addition of the zirconium compound but preferably an alkali is added to the mixture of all three essential ingredients. Typically an alkali metal hydroxide or ammonium hydroxide can be used to raise the pH to a value between 7.5 and 10.5.

As mentioned hereinbefore the organo metallic compounds of the present invention are of use as cross-linking agents in fracturing fluids employed in the hydraulic fracturing of oil or gas-containing subterranean strata to release the oil or gas for recovery. The fracturing fluids are based on so-called solvatable polysaccharides.

Examples of solvatable polysaccharides useful herein include the galactomannan gums, glucomannan gums, and cellulose derivatives. Solvatable galactomannan gums and glucomannan gums are naturally occurring; however, cellulose is rendered solvatable by reacting cellulose with hydrophilic constituents.

The galactomannan gums and glucomannan gums can also be reacted with hydrophilic constituents to thereby produce gelling agents useful herein.

Solvatable polysaccharides having molecular weights of less than about 100,000 do not form cross-linked gels which are useful herein. The most preferred solvatable polysaccharides useful herein have molecular weights in the range of from about 200,000 to about 300,000.

Guar gum, locust bean gum, karaya gum, sodium carboxy methylguar, hydroxyethylguar, sodium carboxymethylhydroxyethyl guar, hydroxypropylguar, sodium carboxymethylhydroxypropylguar, sodium carboxymethylcellulose, sodium carboxymethylhydroxyethy cellulose, and hydroxyethylcellulose are examples of gelling agents useful herein. The hydroxyethylcellulose derivatives used as gelling agent should be those having between 0.5 and about 10 moles of ethylene oxide per anhydroglucose unit. The preferred solvatable polysaccharides are guar gum, hydroxypropylguar and sodium carboxymethyl-hydroxypropylguar. The most preferred solvatable polysaccharide is hydroxypropylguar.

Usually the solvatable polysaccharide is dissolved in a solvent which can be water or an aqueous alcoholic solution e.g. aqueous methanol or aqueous ethanol to which is added the cross-linking agent at an appropriate time and in an appropriate amount. Amounts of solvatable polysaccharide that can be used in the fluid can be up to 1.5 weight per cent based on the weight of aqueous liquid but preferably from 0.3 to about 0.7 weight per cent. Amounts of the organo-metallic compounds cross-linking agent which can be used can be up to 1.3 weight per cent of the aqueous liquid in the fracturing fluid but preferably the amount is from 0.5 to 0.8 weight per cent.

The invention is illustrated in the following Examples.

EXAMPLE 1

Zr/malic acid/sorbitol = 1/2/1

A solution was prepared by dissolving 17.25 g dl-malic acid and 11.72 g sorbitol in 50 g distilled water. To this pale yellow solution were added 15.0 g $ZrCl_4$ over 2 to 5 minutes. The solution temperature rose to about 50° C. After stirring for 15 minutes a clear yellow liquid was obtained. To this solution were then slowly added 60 g of a 33% aqueous NaOH solution. This was again accompanied by a temperature rise during the addition time of two to five minutes. During the addition a creamy precipitate was observed to from at pH 1-2 which redissolved at pH 2-8 and resulted finally in a clear pale yellow solution at pH 9.5 with a Zr content of 3.80%.

EXAMPLE 2

Zr/malic acid/sorbitol = 1/2/2

A solution was prepared by dissolving 17.25 g dl-malic acid and 23.44 g sorbitol in 50 g distilled water. To this solution were slowly added 15.0 g $ZrCl_4$ and the solution stirred for 15 mins. The resulting product was clear yellow liquid. On addition of about 60 g of a 33% aqueous NaOH solution the yellow colour faded to give a colourless solution at pH 1-2 but then reappeared at pH 4-8 and resulted in a straw coloured final product at pH 9-9.5 with a Zr content of 3.62%.

EXAMPLE 3

Zr/malic acid/sorbitol = 1/2/1.5

A solution was prepared by dissolving 17.25 g dl-malic acid and 17.58 g sorbitol in 50 g $H_2O$. To this solution was slowly added 15.0 g $ZrCl_4$ and the solution stirred for 15 mins. The resulting product was a clear yellow liquid. On addition of about 60 g of a 33% aqueous NaOH solution the yellow colour was initially discharged but then reappeared to give a straw coloured product at pH 9-10 (Zr content = 3.69%).

EXAMPLE 4

Zr/malic acid/sorbitol = 1/2/1

A solution was prepared by dissolving 18.36 g dl-malic acid and 12.46 g sorbitol in 30 g distilled water. To this were then added 41.92 g of an aqueous $ZrOCl_2$ solution (Zr content = 14.9% wt). A clear yellow solution resulted. To this was then added sufficient 33% aqueous NaOH to raise the pH of the product to 10. A clear pale yellow liquid resulted which gradually thickened and gelled to a solid between 2 and 10 minutes after addition.

EXAMPLE 5

Zr/malic acid/sorbitol = 1/1/1

A solution was prepared by dissolving 9.18 g dl-malic acid and 12.46 g sorbitol in 30 g distilled water. To this were then added 41.92 g of an aqueous $ZrOCl_2$ solution (Zr content = 14.9%). A clear yellow solution resulted to which about 60 g of a 33% aqueous NaOH solution were then added. A white gel solid formed at pH 1-3, dissolved at pH 4-8 to produce is a clear pale yellow solution at pH 12. The sample thickened and gelled to a solid in 4-6 hrs.

EXAMPLE 6

Zr/citric acid/sorbitol = 1/2/1

A solution was prepared by dissolving 24.72 g anhydrous citric acid and 11.72 g Sorbitol in 40 g distilled water. To this solution were slowly added 15.0 g $ZrCl_4$ and the solution stirred for 15 minutes. To the resulting clear yellow solution were added 66.61 g of an aqueous 33% solution. On addition the yellow colour faded at pH 1 the reappeared as the pH was raised to 9.5. (Zr content = 3.54%.)

EXAMPLE 7

Zr/citric acid/sorbitol = 1/1.5/1

A solution was prepared by dissolving 18.54 g anhydrous citric acid and 11.72 g sorbitol in 40 g distilled water. To this solution were slowly added 15.0 g $ZrCl_4$ and the solution stirred for 15 minutes. To the resulting clear yellow solution were slowly added 64.88 g of a 33% aqueous NaOH solution. The final, clear, pale yellow product had a pH of 9.5 (Zr content = 3.68%).

EXAMPLE 8

Zr/lactic acid/sorbitol = 1/3/1

A solution was prepared by dissolving 11.72 g sorbitol in 25 g distilled water and adding 19.75 g of a aqueous 88% lactic acid solution. To this clear colourless solution were slowly added 15.0 g $ZrCl_4$ resulting in a hazy yellow liquid. 59.6 g of an aqueous 33% NaOH solution were added. A clear gel formed at pH 4 which redissolved on continued addition to give a clear viscous, pale yellow solution at pH 10 (Zr content of 4.14%).

EXAMPLE 9

Zr/lactic acid/sorbitol = 1/4/1

A solution was prepared by dissolving 11.72 g Sorbitol in 25 g distilled water and adding 26.60 g of an aqueous 88% lactic acid solution. To this clear solution were added 15.0 g $ZrCl_4$. 68.0 g of aqueous 33% NaOH solution were added in total, resulting in a viscous, clear pale yellow solution via a creamy white precipitate/gel (Zr content=4.20%).

EXAMPLE 10

Zr/lactic acid/sorbitol=1/3/2

A solution was prepared by dissolving 23.44 g sorbitol in 40 g distilled water then adding 19.75 g of an aqueous 88% lactic acid solution. To this were then slowly added 15.0 g $ZrCl_4$ and the solution stirred for 15 mins. On addition of an aqueous 33% NaOH solution a clear gel was formed which then redissolved leaving a viscous pale yellow solution at a pH of 12. (Zr content=3.20%).

EXAMPLE 11

Zr/malic acid/glycerol=1/2/1

A solution was prepared by dissolving 17.25 g dl-malic acid in 30 g distilled water and adding 5.92 g glycerol. To this solution was slowly added 15.0 g $ZrCl_4$ and the solution stirred for 15 mins. To the resulting hazy yellow liquid were added 52.4 g of a 33% aqueous NaOH solution. On addition, the yellow colour was discharged and the reappeared at pH 4. The final solution was clear, pale yellow and had a pH of 9.5. (Zr content=4.77%).

TESTING IN HYDROXYPROPYL GUAR (HPG) SOLUTION

Method 2.40 g WG11 HPG powder were rapidly added to 500 ml distilled water in a one liter beaker on a stirrer/hot plate. A few drops of HCl were added to lower the pH to 6.5. The solution was then stirred at slow speed for ½hr to allow the HPG to wet in. About 0.3 g $Na_2CO_3$ were then added to raise the pH to 10 followed by 1 to 3 ml of the aqueous cross-linker with rapid stirring. If no gel formed over a set time at room temperature then heat was applied at a set rate and the temperature of gelation noted. The HPG solution was considered gelled when the magnetic stirrer could no longer function.

The range of samples tested including a number of the products of previous Examples are identified in Table 1:

TABLE 1

Composition of Selected Aqueous Zr/α-hydroxy carboxylic acid/polyol cross-linkers (molar ratios)

| Sample | 1 | 2 | 3 | 4 | 5 | 6 | 7 | 8 | 9 |
|---|---|---|---|---|---|---|---|---|---|
| Example Number | 9 | 11 | 1 | — | — | 7 | 3 | — | — |
| Zr | 1.00 | 1.00 | 1.00 | 1.00 | 1.00 | 1.00 | 1.00 | 1.00 | 1.00 |
| dl-malic acid | | 2.00 | 2.00 | 2.00 | 2.00 | | 2.00 | 2.00 | 2.00 |
| citric acid | | | | | | 1.50 | | | |
| lactic acid | 4.00 | | | | | | | | |
| glycerol | | 1.00 | | | | | | | |
| sorbitol | 1.00 | | 1.00 | 1.19 | 1.28 | 1.00 | 1.50 | 1.65 | 1.75 |

Samples 4, 5, 8 and 9 were products prepared according to the method of Example 1. Their composition varied only in the amount of sorbitol they contained.

TABLE 2

Gelling Characteristics of the Zr/α-hydroxycarboxylic acid/polyol Aqueous Cross-linkers in Hydroxypropylguar

| Sample | Zr content % | Sorbitol/Zr molar ratio | Time at room temperature (mins) | Temperature of gelation |
|---|---|---|---|---|
| 1 | 4.20 | 1.00 | 2 | room temperature |
| 2 | 4.77 | 1.00 | 2 | room temperature |
| 3 | 3.80 | 1.00 | 15 | 25–80° C. |
| 4 | 3.79 | 1.19 | 20 | 45–50° C. |
| 5 | 3.74 | 1.28 | 15 | 65–75° C. |
| 5 repeat | 3.74 | 1.28 | 60 | 70–75° C. |
| 6 | 3.68 | 1.00 | 15 | 65–75° C. |
| 7 | 3.69 | 1.50 | 30 | 65–75° C. |
| 8 | 3.62 | 1.65 | 15 | 70–85° C. |
| 9 | 3.60 | 1.75 | 15 | 90° C. |

These results clearly illustrate the effectiveness of the combination of Zr/αhydroxycarboxylic acid/polyol for controlled delay in cross-linking water soluble polymers suitable for hydraulic fracturing. Cross-linking can be brought about after a suitable time delay or temperature rise has been achieved. Hence they offer improved control and greater flexibility and in addition, their preparation is both simple and straight forward requiring no external heating or complicated additions of base.

We claim:

1. An organo-metallic compound comprising a reaction product of (a) a zirconium compound selected from the class consisting of zirconium halides and zirconium oxyhalides, (b) at least one selected from the group consisting of polyhydroxy alcohols and monosaccharides and (c) at least one alpha-hydroxy carboxylic acid.

2. An organo-metallic compound according to claim 1 in which the said zirconium halide is zirconium tetrachloride.

3. An organo-metallic compound according to claim 1 in which the said alpha-hydroxy carboxylic acid is selected from the class consisting of monocarboxylic acids, dicarboxylic acids and tricarboxylic acids.

4. An organo-metallic compound according to claim 1 in which the said alpha-hydroxy carboxylic acid contains more than one hydroxy group.

5. An organo-metallic compound according to claim 1 in which the said alpha-hydroxy carboxylic acid is lactic acid, malic acid or citric acid.

6. An organo-metallic compound according to claim 1 in which the molar ratio alpha-hydroxy carboxylic acid:zirconium is from 2:1 to 6:1.

7. An organo-metallic compound according to claim 1 in which the molar ration alpha-hydroxy carboxylic acid:zirconium is from 2:1 to 4:1.

8. An organo-metallic compound according to claim 5 in which the said alpha-hydroxy carboxylic acid is lactic acid and the molar ratio lactic acid:zirconium is from 3:1 to 6:1.

9. An organo-metallic compound according to claim 5 in which the said alpha-hydroxy carboxylic acid is citric acid and the molar ratio citric acid:zirconium is 1.5:1 to 2.5:1.

10. An organo-metallic compound according to claim 1 in which the said alpha-hydroxy carboxylic acid is a hydroxy aromatic acid.

11. An organo-metallic compound according to claim 1 in which the said polyol contains at least three hydroxy groups.

12. An organo-metallic compound according to claim 11 in which the said polyol is a monosaccharide.

13. An organo-metallic compound according to claim 1 in which the said polyol is sorbitol.

14. An organo-metallic compound according to claim 1 in which the molar ratio of said polyol:zirconium is from 0.25:1 to 4:1.

15. An organo-metallic compound according to claim 13 in which the molar ratio sorbitol:zirconium is from 0.25:1 to 2:1.

16. An organo-metallic compound according to claim 11 in which the said polyol is glycerol and the molar ratio polyol:zirconium is from 0.5:1 to 4:1.

17. A composition suitable for use as a fracturing fluid for the hydraulic fracturing of oil or gas-containing subterranean strata comprising a solvatable polysaccharide and at least one of the organo-metallic compounds of claim 1.

18. A composition according to 17 in which the said solvatable polysaccharide is selected from the class consisting of galactomannan gums, glucomannan gums and cellulose derivatives.

19. A composition according to claim 17 in which the said solvatable polysaccharide is a hydrophilic derivative of a galactomannan gum or a hydrophilic derivative of a glucomannan gum.

20. A composition according to claim 17 where the said solvatable polysaccharide is hydroxypropylguar.

21. A composition according to claim 17 in which the said solvatable polysaccharide has a molecular weight in the range of from about 200,000 to about 300,000.

22. A composition according to claim 17 containing also a solvent which is selected from the class consisting of water and aqueous solutions of alcohols.

23. A composition according to claim 20 in which the amount of solvatable polysaccharide is up to 1.5 weight per cent based on weight of aqueous liquid.

24. A composition according to claim 22 in which the amount of solvatable polysaccharide is from 0.3 to about 0.7 weight per cent based on weight of aqueous liquid.

25. A composition according to claim 22 in which the organo-metallic compound is present in an amount of up to 1.3 weight per cent based on weight of aqueous liquid.

26. A composition according to claim 22 in which the amount of organo-metallic compound is from 0.5 to 0.8 weight per cent based on weight of aqueous liquid.

* * * * *

UNITED STATES PATENT AND TRADEMARK OFFICE
CERTIFICATE OF CORRECTION

PATENT NO. : 5,089,149
DATED : February 18, 1992
INVENTOR(S) : John Ridland & David A. Brown It is certified that error appears in the above-identified patent and that said Letters Patent is hereby corrected as shown below:

Col. 6, line 4, before "selected" insert --polyol--.

Signed and Sealed this

Fifteenth Day of June, 1993

Attest:

MICHAEL K. KIRK

*Attesting Officer*   *Acting Commissioner of Patents and Trademarks*